United States Patent [19]

Sofranko et al.

[11] 4,448,985
[45] May 15, 1984

[54] OXIDATION OF ISOBUTYRIC ACID TO ALPHA-HYDROXYISOBUTYRIC ACID

[75] Inventors: John A. Sofranko, West Chester; John J. Leonard, Springfield, both of Pa.

[73] Assignee: Atlantic Richfield Company, Los Angeles, Calif.

[21] Appl. No.: 449,301

[22] Filed: Dec. 13, 1982

[51] Int. Cl.³ ............................................. C07C 59/00
[52] U.S. Cl. ..................................................... 562/579
[58] Field of Search ......................... 562/579; 568/910

[56] References Cited

U.S. PATENT DOCUMENTS 2,971,981 2/1961 Aries ................................... 562/579
3,198,823 8/1965 Akaberyashi et al. .............. 562/579
3,284,494 11/1966 Schoenbrunn ...................... 568/910

FOREIGN PATENT DOCUMENTS 470216 12/1950 Canada ................................ 568/910

*Primary Examiner*—Paul J. Killos
*Attorney, Agent, or Firm*—Delbert E. McCaslin

[57] ABSTRACT

A process for the preparation of alpha-hydroxyisobutyric acid by the stoichiometric oxidation of isobutyric acid in aqueous solution at temperatures of from about 50° C. to 200° C. in the presence of a thallic ($Tl^{+3}$) salt.

8 Claims, No Drawings

OXIDATION OF ISOBUTYRIC ACID TO ALPHA-HYDROXYISOBUTYRIC ACID

BACKGROUND OF THE INVENTION

Alpha-hydroxyisobutyric acid has been prepared by oxidizing an aqueous solution of the corresponding alcohol in the presence of a base and a platinum catalyst as shown for example in C. K. Heyns and H. Paulsen, "Newer Methods of Preparative Organic Chemistry" Vol. II, pp. 303 (1963).

As described in an article by E. F. Schoenbrunn and J. H. Gardner, J. Am. Chem. Soc., Vol. 82, pp. 4905 (1960) and U.S. Pat. Nos. 2,847,453, 2,847,454 and 2,847,465 α-hydroxyisobutyric acid may be produced by the liquid phase oxidation of isobutylene with nitrogen tetroxide and nitric acid.

An article by E. C. Taylor, H. W. Artland and G. McGillivray, Tetrahedron Letters, No. 60, pp. 5285–5288 (1970) discloses the preparation of for example, α-isobutoxyiso-butyric acid using thallium (III) acetate with an excess of neat isobutyric acid to prepare a thallium (III) carboxylate and acetic acid with removal of the acetic acid by distillation and reflux under nitrogen of the thallium (III) carboxylate in an isobutyric acid solvent to give the α-acyloxycarboxylic acid.

U.S. Pat. No. 3,897,489 discloses a method for the production of alpha-hydroxyisobutyric acid by the catalytic oxidation of isobutylene glycol with molecular oxygen in the presence of a supported platinum catalyst.

The process of the present invention provides a high yield selectivity to the α-hydroxyisobutyric acid by the stoichiometric oxidation of isobutyric acid with thallic salts. Isobutyric acid is readily available from oxidation of isobutyraldehyde obtained for example as a by-product in n-butyraldehyde/n-butanol production.

The α-hydroxyisobutyric acid product of this invention may be dehydrated to methacrylic acid by known methods, as shown for example in U.S. Pat. No. 3,562,320 (1971), or reacted with methanol to give methyl methacrylate directly as described in British Pat. No. 852,664.

SUMMARY OF THE INVENTION

According to the present invention there is provided an improved oxidation process for the preparation of α-hydroxyisobutyric acid by heating stoichiometric amounts of isobutyric acid, water and a thallic salt.

It is an object of this invention to provide an improved process for the preparation of alpha-hydroxyisobutyric acid by the stoichiometric oxidation of isobutyric acid.

It is another object of this invention to provide a novel reaction system useful in the conversion of isobutyric acid to α-hydroxyisobutyric acid.

A further object is to provide a specific mechanism for the employment of thallium (III) salts and water in a stoichiometric oxidation process for preparing α-hydroxyisobutyric acid.

These and other objects and advantages of this invention will become apparent from the description of the invention which follows and from the claims.

DESCRIPTION OF THE INVENTION

In accordance with this invention, alpha-hydroxyisobutyric acid is produced by heating at temperatures of from 50° C. to 200° C., preferably 75° C. to 150° C., under liquid phase conditions, stoichiometric quantities of isobutyric acid, water and a thallic ($Tl^{+3}$) salt conforming to the general formula $TlX_3$ wherein X is $Cl^-$, $Br^-$, $NO_3^-$, $CF_3COO^-$ or $C_6H_5COO^-$ or halogen and lower alkyl ($C_1$ to $C_4$) substituted thallium (III) benzoates. Thallium (III) sulfate, $Tl_2(SO_4)_3$ may also be employed. Thallic acetate, or compounds having a hydrogen attached to the α-carbon cannot be employed as they will oxidize.

A general postulated equation for the reaction may be represented as follows:

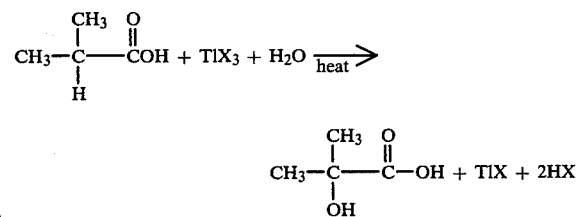

The reaction may be carried out in any suitable reactor which is generally equipped with a means for agitation and a means for regulating temperature. Although the order of addition of the reactants may vary, a general procedure for carrying out the reaction is to charge the proper stoichiometric quantities of an aqueous solution of isobutyric acid into the reaction vessel and then add the molar equivalent amount of a $TlX_3$ compound calculated according to the above equation and heat the mixture to the desired temperature with stirring for the appropriate reaction period. The reaction may be carried out as a batch or continuous process and the reaction products recovered and treated by any conventional method such as filtration to remove insoluble TlX formed.

The isobutyric acid employed in the process of the invention which may be obtained, for example, by the oxidation of isobutyraldehyde should be relatively pure and not contain any appreciable amount of contaminants such as n-butanol, butyric acid, etc. which would affect the reaction.

The thallium salts employed in the stoichiometric oxidation process of the present invention are in the $Tl^{+3}$ oxidation state and may be organic or inorganic thallium (III) compounds. Representative chemical forms of the thallium (III) salt compounds which can be used as such or as mixtures include for example organic thallium compounds such as thallium (III) benzoate $(Tl(OBz)_3)$ which may be halogen or lower alkyl (C1-C4) substituted and thallium (III) trifluoroacetate, etc. and inorganic thallium compounds such as thallic bromide, chloride, nitrate, sulfate, oxide, etc.

The thallium (III) salt employed may be in a homogeneous state in the reaction mixture at reaction conditions. Thus, the compound may be present in solution or suspension and may also be on support materials which will not affect the reaction such as alumina, silica gel, activated carbon or zeolites. The compounds may be partially or completely soluble under reaction conditions and are preferably in a finely divided state. The reaction is carried out in the presence of a stoichiometric proportion of the thallic salt based on the conversion of isobutyric acid, water and the thallic salt to α-hydroxyisobutyric acid as may be calculated according to the reaction equation set forth hereinabove. In the stoichiometric reactions, the high equivalent weight of the thallium (III) salts limit the maximum isobutyric acid concentration to about 20 weight percent + or −5 weight percent.

Although not required in the reaction, solvents which contain no functional groups oxidizable in the reaction system such as for example sulfolane and diphenyl ether may be employed.

Reaction times are generally dependent upon the temperature of reaction, which may range from about 50° C. to 200° C., preferably 75° C. to 150° C. and the thallic oxidizing salt being charged as well as the type of equipment being employed. Usually between ½ hour and 4 hours at reaction temperatures are required to obtain the desired degree of reaction but shorter and longer times may be employed. Reaction times will vary dependent on whether the process is continuous or batch.

The following examples are provided to illustrate the invention in accordance with the principles of this invention but are not to be construed as limiting the invention in any way except as indicated by the appended claims.

EXAMPLES 1–10

In Examples 1–10 which follow in Table form, an aqueous solution of isobutyric acid (IBA) was prepared by weighing the desired quantities of the isobutyric acid and water into a 500 ml round bottom glass reaction flask equipped with a mechanical stirrer, a thermometer and reflux condenser. A molar equivalent quantity of a TlX$_3$ salt compound, calculated according to the above-mentioned reaction formula, was added and the reaction mixture heated on an oil bath to the desired temperature with stirring for the desired time. The contents of the flask were then cooled and filtered to remove any insoluble TlX. The filtrate was titrated for unconverted Tl$^{+3}$ and the product α-hydroxyisobutyric acid (α HIBA) determined by high pressure liquid chromatographic analysis. The α-hydroxyisobutyric acid yield (mol percent) is calculated as follows:

$$\text{HIBA Yield} = \frac{\text{mole HIBA detected}}{\text{mole Tl}^{+3} \text{ converted}}$$

TABLE

| Ex. No. | Tl$^{+3}$ Salt (Wt. %) | IBA (Wt. %) | Temp. (°C.) | Time (hrs.) | Tl$^{+3}$ (% Conversion) | HIBA (mol %) Yield |
|---|---|---|---|---|---|---|
| 1 | TlCl$_3$ (35) | 10.0 | 90 | 2.5 | 19.5 | 19 |
| 2 | TlCl$_3$ (35) | 10.0 | 140 | 1.0 | 23.0 | 22 |
| 3 | TlCl$_3$ (3.5) | 1.0 | 120 | 12.5 | 5.0 | 4 |
| 4 | Tl(NO$_3$)$_3$ (44) | 10.0 | 90 | 2.5 | 85.0 | 84 |
| 5 | Tl(NO$_3$)$_3$ (10) | 2.3 | 125 | 2.5 | 39.0 | 37 |
| 6 | TlBr$_3$ (15) | 3.0 | 140 | 3.0 | 20.0 | 18 |
| 7 | TlBr$_3$ (15) | 3.0 | 100 | 3.5 | 15.0 | 10 |
| 8 | Tl(OBz)$_3$ (15) | 2.5 | 125 | 2.5 | 10.0 | 8 |
| 9 | Tl$_2$(SO$_4$)$_3$ (13) | 2.3 | 125 | 2.5 | 41.0 | 39 |
| 10 | Tl(CF$_3$COO)$_3$ (20) | 3.2 | 125 | 2.5 | 80.0 | 76 |

We claim:

1. A process for the preparation of α-hydroxyisobutyric acid which comprises heating at temperatures of from about 50° C. to 200° C. a mixture containing stoichiometric quantities of isobutyric acid, water and a TlX$_3$ salt selected from the group consisting of thallic chloride, thallic bromide, thallic nitrate, thallic oxide, thallic sulfate, thallium (III) trifluoroacetate and thallium (III) benzoate.

2. A process according to claim 1 wherein the TlX$_3$ salt is thallic chloride.

3. A process according to claim 1 wherein the TlX$_3$ salt is thallic bromide.

4. A process according to claim 1 wherein the TlX$_3$ salt is thallic nitrate.

5. A process according to claim 1 wherein the TlX$_3$ salt is thallium (III) trifluoroacetate.

6. A process according to claim 1 wherein the temperature is in the range of from 75° C. to 150° C.

7. A process according to claim 1 wherein the TlX$_3$ salt is supported.

8. A process according to claim 1 wherein an inert solvent containing no functional group oxidizable in the reaction is employed.

* * * * *